(12) United States Patent
Curcio

(10) Patent No.: US 8,394,336 B2
(45) Date of Patent: Mar. 12, 2013

(54) BIOCHEMICAL ASSAY

(75) Inventor: Mario Curcio, Sins (CH)

(73) Assignee: Roche Diagnostics Operations, Inc., Indianapolis, IN (US)

(*) Notice: Subject to any disclaimer, the term of this patent is extended or adjusted under 35 U.S.C. 154(b) by 0 days.

(21) Appl. No.: 11/260,913

(22) Filed: Oct. 28, 2005

(65) Prior Publication Data

US 2006/0099719 A1 May 11, 2006

(30) Foreign Application Priority Data

Nov. 5, 2004 (EP) .................................. 04026314

(51) Int. Cl.
*G01N 27/00* (2006.01)

(52) U.S. Cl. ........ 422/408; 436/518; 436/164; 436/169; 436/172; 422/400; 422/401; 422/412; 422/425; 435/7.1; 435/283.1; 435/287.1; 435/287.7; 435/288.7

(58) Field of Classification Search .............. 422/55–58, 422/61, 68.1, 101, 400, 401, 408, 412, 425; 435/287.1, 287.2, 287.3, 287.6, 287.7, 287.9, 435/288.7, 4, 7.1, 283.1; 436/501, 66, 67, 436/518, 164, 169, 172
See application file for complete search history.

(56) References Cited

U.S. PATENT DOCUMENTS

| | | | |
|---|---|---|---|
| 4,094,647 A | 6/1978 | Deutsch et al. | |
| 4,145,406 A | 3/1979 | Schick et al. | |
| 4,235,601 A | 11/1980 | Deutsch et al. | |
| 4,361,537 A | 11/1982 | Deutsch et al. | |
| 4,366,241 A | 12/1982 | Tom et al. | |
| 4,521,518 A * | 6/1985 | Carter et al. | 436/10 |
| 4,632,901 A * | 12/1986 | Valkirs et al. | 435/5 |
| 4,740,468 A | 4/1988 | Weng et al. | |
| 4,774,174 A | 9/1988 | Giegel et al. | |
| 4,806,311 A | 2/1989 | Greenquist | |
| 4,806,312 A | 2/1989 | Greenquist | |
| 4,806,487 A * | 2/1989 | Akers et al. | 436/93 |
| 4,879,215 A | 11/1989 | Weng et al. | |

(Continued)

FOREIGN PATENT DOCUMENTS

| | | |
|---|---|---|
| EP | 0271204 A2 | 6/1988 |
| EP | 0279574 B1 | 8/1988 |
| EP | 0863401 B1 | 9/1998 |
| EP | 0864865 B1 | 8/2001 |
| JP | 5126832 A1 | 5/1993 |
| JP | 11133027 A1 | 5/1999 |
| WO | WO9221980 A1 | 12/1992 |
| WO | 03012426 A1 | 2/2003 |
| WO | WO 2004/042364 A2 | 5/2004 |

OTHER PUBLICATIONS

Wikipedia Online Website, "Hemoglobin" downloaded from url: <http://en.wikipedia.org/w/index.php?title=Hemoglobin& printable=yes> on Aug. 2, 2006.*
Wikipedia Online Website, "Chemical polarity" downloaded from url: <http://en.wikipedia.org/w/index.php?title=Chemical_polarity& printable=yes> on Aug. 2, 2006.*

*Primary Examiner* — Melanie Y Brown

(74) *Attorney, Agent, or Firm* — McDonnell Boehnen Hulbert & Berghoff LLP

(57) ABSTRACT

A biochemical assay is provided comprising a substrate being capable of binding at least a target analyte and eventually other constituents contained in a biological sample, a test zone on the substrate for sample application, a non-immobilized conjugate reagent provided in the test zone for labeling the analyte, the conjugate reagent being capable of specific binding to the analyte but remaining unbound to the substrate, and a flow path for transporting a washing liquid through the test zone and washing an excess of unbound conjugate reagent away from the test zone. The test zone is also a detection area for detecting the labeled analyte.

31 Claims, 2 Drawing Sheets

U.S. PATENT DOCUMENTS

| | | | |
|---|---|---|---|
| 4,956,302 A | | 9/1990 | Gordon et al. |
| 4,994,238 A | * | 2/1991 | Daffern et al. ................ 422/422 |
| 5,212,065 A | * | 5/1993 | Pegg et al. ..................... 435/7.9 |
| 6,007,999 A | * | 12/1999 | Clark ............................. 435/7.1 |
| 6,159,747 A | * | 12/2000 | Harttig et al. ................ 436/518 |
| 6,162,645 A | | 12/2000 | Lee et al. |
| 6,399,293 B1 | | 6/2002 | Pachl et al. |
| 2002/0064888 A1 | * | 5/2002 | Maynard et al. .............. 436/518 |
| 2002/0164811 A1 | * | 11/2002 | Hud et al. ....................... 436/67 |
| 2003/0040021 A1 | * | 2/2003 | Clark et al. .................... 435/7.9 |
| 2003/0129680 A1 | * | 7/2003 | O'Connor, Jr. ............. 435/7.32 |
| 2003/0170881 A1 | | 9/2003 | Davis et al. |
| 2007/0190658 A1 | * | 8/2007 | McCroskey et al. ........... 436/67 |

\* cited by examiner

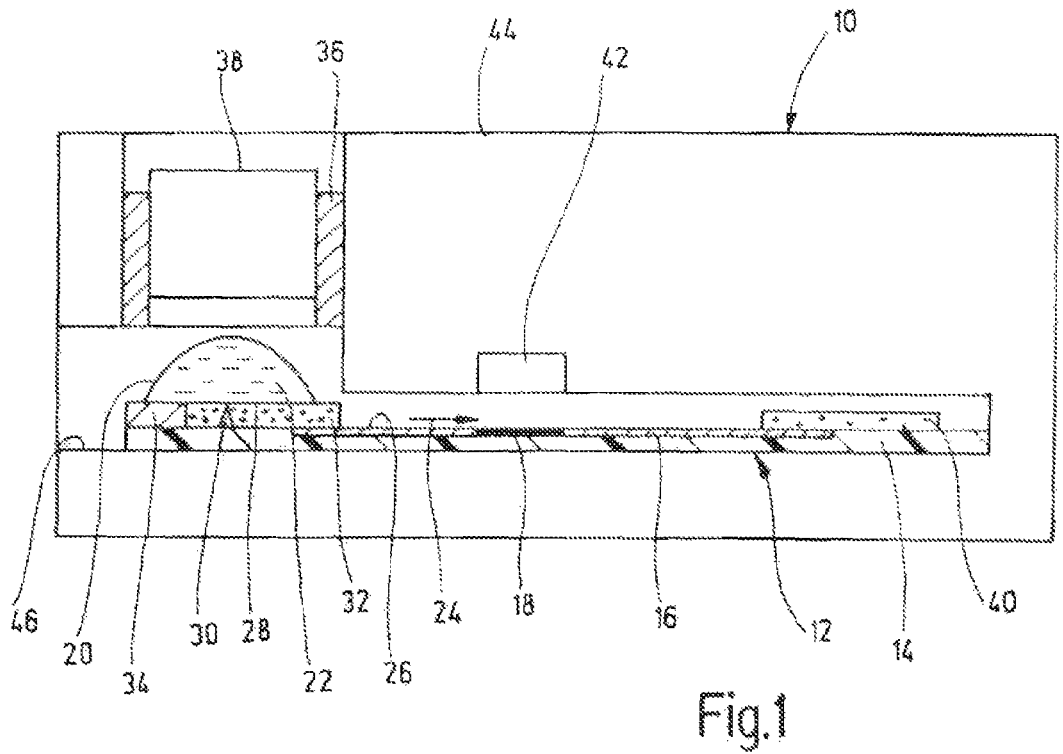
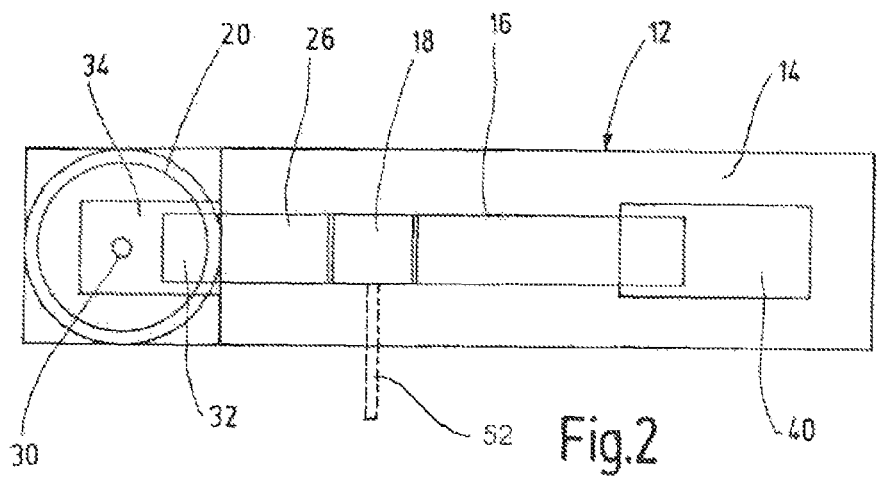

BIOCHEMICAL ASSAY

BACKGROUND OF THE INVENTION

The invention concerns a biochemical assay and a process for determining at least one target analyte in a biochemical sample, typically glycated and total haemoglobin in a blood sample. The invention also concerns an analytical test element on the basis of such a biochemical assay.

The glycation of haemoglobin is increased in the blood of diabetes patients. The increase depends on the concentration of glucose, free to move through the erythrocyte membrane and the period of incubation of the protein with glucose, via a non-enzymatic reaction. Hence, the determination of glycated haemoglobin (namely HbA1c) allows a retrospective estimate of the average glucose concentration and thus of the quality of the metabolic control of the diabetic patient. The disappearance of HbA1c from the blood depends on the lifetime of the erythrocytes (the average lifetime of these cells is about 120 days with a half-life of 60 days). HbA1c is defined as haemoglobin A that has been glycated by glucose with a slow but irreversible reaction on the N-terminal valine residues of the $\beta$ chains. The HbA1c value is usually stated as a percentage of the total haemoglobin which requires a determination of the haemoglobin concentration from the same blood sample in addition to the HbA1c content.

In connection to this, it is already known to use test elements in order to provide a simple handling and rapid determination. A test element is generally understood as a carrier-bound (micro) system which enables sample preparation for an immediate analysis independent of a laboratory environment. Such test elements are usually intended to be single-use articles or disposables for near patient diagnostics in which all reagents that are necessary to carry out the test are provided on the carrier or component so that they can be used without requiring special handling.

In this context, U.S. Pat. No. 6,399,293 B1 discloses a teststrip-based system comprising a sample application zone, a reagent zone containing non-immobilized signal-generating molecules, a separation zone for separating the excess signal-generating molecules that are not bound to glycated haemoglobin and a detection zone. The separation occurs by means of a positively charged membrane binding only the excess of a negatively charged signal-generating ligand in the separation zone. The total haemoglobin including the labeled HbA1c will not be bound to the membrane and thus can be transported through the different zones within the sample liquid.

More generally, the use of test elements for different binding assays is well-known. For example, U.S. Pat. No. 4,094,647 describes a device that comprises a material capable of transporting a solution by capillary action. Different zones on the strip contain the reagents needed to perform the binding assay and to produce a detectable signal as the analyte is transported through the zones. The binding reaction occurs between an antigen and a complementary antibody. Many variations of the method have followed. However, despite all the activity in this field, methods have been developed always in the same direction involving the use of some immobilized reagent, mostly antibody, resulting in higher effort and costs for reagents and chemistry integration, and/or involving a chromatographic run, generally requiring the need for the analyte to go through several steps in space and time to meet the reaction and detection conditions.

SUMMARY OF THE INVENTION

It is against the above background that the present invention provides certain unobvious advantages and advancements over the prior art. In particular, the inventor has recognized a need for improvements in biochemical assay design.

Although the present invention is not limited to specific advantages or functionality, it is noted that the present invention reduces the assay complexity, minimizes the necessary sample amount, uses less reagents, and avoids in particular immobilization and immunochemistry, while maintaining accuracy and reproducibility of the test with ease of handling.

The present invention is based on the idea to overlap application, reaction and detection in one spot of a solid support or substrate. In accordance with one embodiment, a biochemical assay is provided comprising: a substrate being capable of binding at least a target analyte and eventually other constituents contained in a biological sample, a test zone on the substrate for sample application, a non-immobilized conjugate reagent provided in the test zone for labelling the analyte, the conjugate reagent being capable of specific binding to the analyte but remaining unbound to the substrate, and a flow path for transporting a washing liquid through the test zone and washing an excess of unbound conjugate reagent away from the test zone, wherein the test zone is also a detection area for detecting the labelled analyte.

Thereby, several advantages are achieved. The sample application, reaction and detection occur in one and the same spot or zone. Hence, the analytes do not have to be transported meaning that higher reproducibility can be expected. A compact design can be achieved, with minimized reaction and sample volumes, minimized strip length and lower washing volumes. The handling is made easy and no elaborate separation steps are required.

In another typical embodiment of the present invention, an integrated reservoir contains the washing liquid and the reservoir can be fluidly connected to the flow path. According to a further embodiment, the reservoir is connectable to the flow path by an element rupturing a wall of the reservoir.

For a self-controlled transport, in accordance with yet another embodiment, the flow path can be a porous or capillary structure capable to transport the washing liquid by capillary forces. Alternatively, to direct sample application, a microfluidic system can be provided for transport of sample fluid to the test zone.

In accordance with still another embodiment, an adsorbing element can be arranged on the flow path downstream the test zone for taking up liquid waste. Further, the substrate can be a solid phase chromatographic layer that can be on a polymer or metal support. The analyte is typically a protein. The conjugate reagent can be a molecule other than a protein. The size of that molecule can be less than the size of the analyte.

Such a conjugate molecule can consists of a more or less polar organic group as the signalling part and a small organic or inorganic group as the ligand part, which recognizes and binds specifically to the target analyte, like for example boronic acid, a chelating group, a peptide epitope or an oligonucleotide.

The conjugate reagent can have a high coefficient of partition for the washing liquid compared to the substrate. Depending on the conjugate chemical structure, the washing liquid can be an organic solvent, a mixture of water and a miscible organic solvent or just an aqueous solution, can contain a surfactant, and can be buffered at an optimal or predetermined pH, so that the analyte sticks to the substrate while the binding reaction of the conjugate still occurs. Accordingly, the excess of unbound reagent can be removed.

In accordance with yet still another embodiment, the conjugate reagent is provided in dried form in the test zone, which can be provided before the sample application.

The invention also concerns an embodiment comprising an analytical test element, which can be disposable, for a biochemical assay according to the invention, and a device for processing the analytical test element.

In accordance with yet still another embodiment, an analytical test element for determining the ratio of glycated to total haemoglobin in a blood sample is provided comprising: a substrate being capable of binding at least haemoglobin and eventually other constituents contained in a blood sample, a test zone on the substrate for sample application, a non-immobilized conjugate reagent provided in the test zone for labelling glycated haemoglobin, and a flow path for transporting a washing liquid through the test zone and washing an excess of unbound conjugate away from the test zone. The test zone is also a detection area for detecting the labelled and total haemoglobin.

In accordance with yet still another embodiment of the present invention, a process for determining at least one target analyte in a biochemical sample is provided, comprising: providing a substrate being capable of binding at least the target analyte and eventually other constituents contained in the sample, providing a non-immobilized conjugate reagent in the test zone for labelling the analyte, the conjugate reagent being capable of specific binding to the analyte but remaining unbound to the substrate, applying the sample in a finite test zone of the substrate, transporting a washing liquid through the test zone and washing an excess of unbound conjugate reagent away from the test zone, and detecting the labelled analyte in the test zone.

In yet still another embodiment, blood is used as a sample. The target analyte is haemoglobin, specifically glycated haemoglobin. The blood is haemolysed by a haemolysing reagent present typically also in dried form in a suitable substrate, on which total haemoglobin adsorbs. The conjugate reagent also present in dried form in the sample application zone is solubilized by the sample and binds to the glycated haemoglobin. The excess of unbound conjugate reagent is then transported away by the laterally flowing washing liquid. Total haemoglobin and glycated haemoglobin are photometrically detected at different respective wavelengths, so that the ratio of glycated to total haemoglobin can be determined.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood and is elucidated in more detail when read in conjunction with the following drawings, where like structure is indicated with like reference numerals and in which:

FIG. 1 shows a measuring device comprising a test element for a biochemical assay in longitudinal cross-section in accordance with an embodiment of the present invention;

FIG. 2 is a top view of a test element in accordance with an embodiment of the present invention.

Figure 3A:
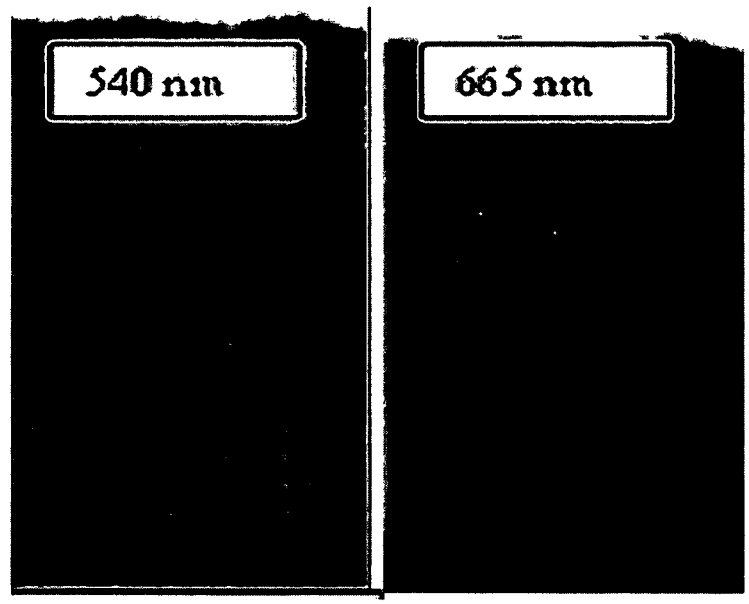
FIGS. 3a and b show test results of an assay in accordance with an embodiment of the present invention, which is carried out on a TLC plate of standard format.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiments of the present invention.

DETAILED DESCRIPTION OF THE INVENTION

The measuring device 10 shown in FIG. 1 allows a disposable strip-shaped test element 12 to be processed for determining total haemoglobin and HbA1c values of a blood sample in a single-use test. As further illustrated in FIG. 2, the test element 12, in accordance with one embodiment of the present invention, essentially comprises a carrier 14, a substrate 16 with a test zone 18 formed therein, a reservoir 20 containing a washing liquid 22 and a flow path 24 for the transport of washing liquid through the test zone.

The carrier 14 can be formed as an elongated thin strip of a plastic or metal foil, with a central part where a thin layer of chromatographic material, analogous to a TLC plate, is layered as the substrate 16. The substrate 16 can have a microporous structure 26 serving as the flow path 24 essentially parallel to the longitudinal axis of the strip 14.

The reservoir 20 can comprise a deformable blister which has a bottom wall 28 that can be ruptured or punctured by an integrated barb 30 so that the washing liquid 22 is forced out of the created hole into a soft compressible adsorbing material 32 bordered by a soft compressible U-frame 34. Mechanical actuation can be accomplished by a pressing block 36 for puncturing the blister and a pressing cylinder 38 to push the liquid 22 out.

The adsorbing material 32 overlaps the upstream end of the substrate 16 to enable liquid transfer into the microporous structure 26. An adsorbing element 40 is arranged downstream the test zone 18 for taking up the liquid waste.

As only schematically illustrated in FIG. 2, the linear liquid transport system described so far could be part o a more complex microfluidic system. Instead of direct sample spotting, the sample fluid can reach the test zone from the side through the channel 52 after prior processing. For example, haemolysis of blood and eventually also the binding reaction with the conjugate can take place in zone(s) different from the adsorbing and detection area 18. In this case, care should be typically taken to avoid excess of sample spreading outside the test zone 18. Microfluidic flow control can be used to deliver typically a given amount at the given location.

In order to carry out a photometrical measurement, a detector 42 can be located in the device 10 in correspondence of the test zone 18 of the test element 12. For precise alignment, the housing 44 of the device 10 can have a guide way 46 which allows sliding the test element 12 in and out.

In one example, to perform a test, a small sample volume (μl) of a blood sample to be analysed is delivered to the test zone 18. Fresh capillary blood or whole blood can be used. Release of haemoglobin from the erythrocytes is obtained by action of a haemolysing reagent with which the substrate is impregnated.

The glycated haemoglobin, made accessible in this way, can be selectively labelled by reaction with a non-immobilized conjugate reagent present in the test zone 18. The conjugate can comprise phenylboronic acid linked to an organic dye with maximum absorbance at a wavelength about >600 nm. This selectively binds to the sugar residue of glycated haemoglobin and thus makes it detectable and distinguishable. In order to ensure that the reaction is quantitative, an excess of conjugate relative to the expected amount of glycated haemoglobin is used. Therefore, it is typical that the excess or fraction of conjugate reagent, which is not bound to glycated haemoglobin, is separated after sample application from the test zone 18.

The separation mechanism according to an embodiment of the invention is based upon the principle of immobilizing the analyte(s) in the test zone 18, by simple adsorption whereas the unbound conjugate is removed with the aid of the washing liquid 22. To make this possible, the analyte and the conjugate typically belong to different chemical classes. In accordance with one embodiment, if the analyte is a protein, the conjugate must be something other than a protein. Typically, this is instead a relatively small organic molecule more or less polar.

As outlined above, the non-glycated haemoglobin and the complex of glycated haemoglobin with boronic acid-dye conjugate stick on the TLC substrate firmly under particular washing conditions, while the excess of unbound conjugate is transported away with the mobile washing phase.

It is important for an optimal separating effect that the conjugate has a high coefficient of partition for the washing liquid 22 compared to the substrate 16. Particular attention must be paid to the pH value. This influences, on one hand, the reaction between target analyte and conjugate and, on the other hand, can determine how strongly the analyte adsorbs on the substrate and the affinity of the free conjugate for the mobile phase.

At a given time after sample application, the flow of the washing fluid can be actuated by means of the mechanism 36, 38, so that the liquid is transported through the adsorbing material 32 and the microporous structure 26, passing the test zone 18 and taking up excess conjugate eventually into the waste 40.

In order that the invention may be more readily understood, reference is made to the following examples, which are intended to illustrate the invention, but not limit the scope thereof.

EXAMPLE 1

Figure 3B:
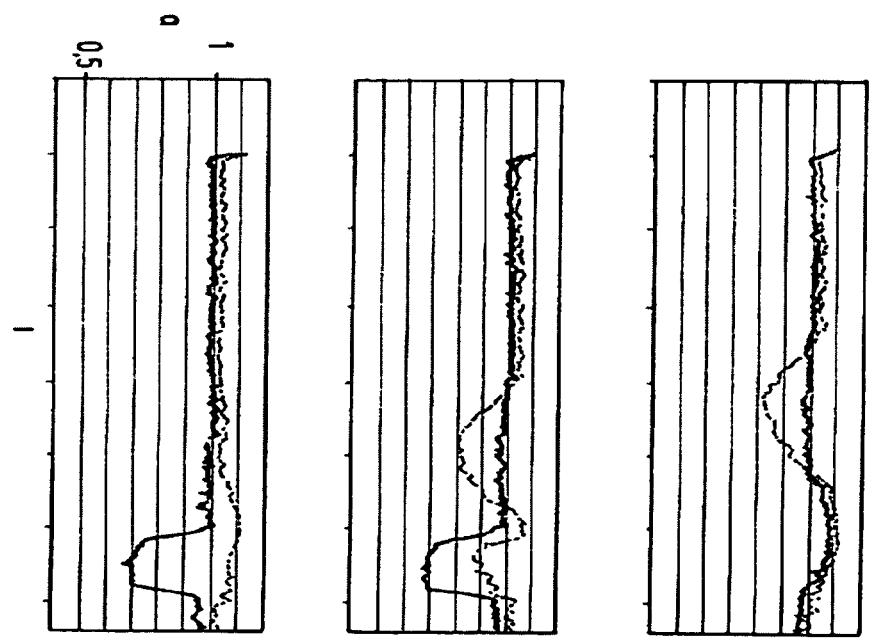

In one working example (FIG. 3) a commercial aluminium oxide TLC plate was used as substrate, phenylboronic acid linked to an organic dye of low-polarity (max. absorbance at ca. 650 nm, emission at ca. 670 nm) as conjugate reagent (MW<700 Dalton), and a buffer phosphate/EDTA at pH typically $\geq 7$, most typically $\geq 9$, containing approximately 1% tetradecyltrimethylammonium bromide (TTAB), as mobile phase, TTAB was used also as haemolysing reagent.

Two controls were run in parallel with the HbA1c test (blood sample containing 10% glycated haemoglobin plus non-immobilized conjugate) in the center, namely blood sample without conjugate on the left, and conjugate without blood on the right. The two images in FIG. 3*a* were taken at different wavelengths, i.e., 540 nm and 665 nm, by using a CCD camera as detector and a set of filters for the illumination source and the camera objective. The three absorbance traces showing relative absorbance a over separation length d in FIG. 3*b* refer to the three spotted samples, aligned in the same order, with the solid line representing 540 nm and the dotted line 665 nm respectively. From here it is clear that total haemoglobin with or without conjugate (absorbing at 540 nm) is strongly adsorbed on the substrate while the non-immobilized and unbound conjugate (detected at 665 nm) is transported away from the application spot under these washing conditions. Only when reaction between conjugate and glycated haemoglobin occurs (spot in the middle) absorbance at 665 nm proportional to the percentage of HbA1c present can be detected in the application zone.

In principle, known methods, i.e., absorbance, reflection or fluorescence can be conducted to determine haemoglobin remaining in the test zone 18. In accordance with an embodiment of the present invention, both total and glycated haemoglobin have to be detected. Use is made of the fact that the boronic acid conjugate has an absorption maximum at a wavelength which is outside of the range in which haemoglobin absorbs. The ratio of glycated to total haemoglobin can then be determined by measuring the reflectance of the test zone 18 at different wavelengths, for example at 540 nm (for the total amount of haemoglobin) and 665 nm (for the dye, which is bound via boronic acid to glycated haemoglobin).

The mechanism by which the analyte of interest sticks while the excess of unbound non-immobilized conjugate reagent is removed from the reaction/detection area under particular washing conditions, can be generalized to most assays in which the analyte is a protein, typically an abundant protein, and the labelled ligand is a non-protein that is something other than an antibody. Typically, this is instead a relatively small organic molecule more or less polar, or a small peptide epitope, or even an oligonucleotide for nucleic acid binding proteins. The substrate can be other than aluminium oxide, like for example silica, reversed phase or other chromatographic material, so that the protein analyte can be firmly adsorbed by electrostatic or hydrophilic interactions, hydrogen bonding, hydrophobic interactions, or combinations thereof. The mobile phase can be a buffer at such pH that the analyte sticks on the solid phase but that the reaction still occurs. It can contain a detergent other than TTAB at any optimal concentration. It can contain acids or bases. It can contain an organic solvent or can be a simple mixture of a miscible organic solvent and water. Pre-spotted samples at known concentration could also be present on the same test strip for direct calibration. If all this is considered, then this method can be used to determine the presence and quantity of antibodies and ligand-binding proteins in a biological fluid, such as blood, urine, milk or in a cell extract, either human tissue or other organisms including bacteria, whenever specific suitable ligands are known and can be derivatized with signal-generating molecules, if not already self-signaling.

It is also contemplated to use different signals for different ligands so that different analytes can be targeted at the same time on the same spots, or for introducing internal calibration standards. For better sensitivity, fluorescence detection is typical. More specific examples of assays that could be performed by this method involve different classes of ligand-binding proteins. Besides immunoglobulines, the following are also contemplated: DNA and RNA binding proteins, lipid-binding proteins (e.g., β-lactoglobulin, serum retinol-binding protein, urinary α2-globuline, fatty acid binding proteins), lectins, serum albumins, pheromone-binding proteins, odor-binding proteins, and immunosuppressant-binding proteins.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims.

More specifically, although some aspects of the present invention are identified herein as preferred or particularly advantageous, it is contemplated that the present invention is not necessarily limited to these preferred aspects of the invention.

What is claimed is:

1. A biochemical assay device for detecting a protein analyte in a biological sample, the device comprising
    a substrate comprising a strip defining a flow path for transporting a washing liquid through a finite zone formed as one spot on the strip defining a sample application area, test zone and detection area that non-specifically binds the analyte,
    a non-immobilized conjugate reagent dried in the finite zone for labeling the analyte, said conjugate reagent being a molecule other than a protein and being capable of specific binding to the analyte but remaining unbound to the substrate, and
    the finite zone can be located in correspondence to a detector for detecting the labeled analyte.

2. The biochemical assay device of claim 1, wherein a reservoir contains the washing liquid and the reservoir can be fluidly connected to the flow path.

3. The biochemical assay device of claim 2, wherein the reservoir is connectable to the flow path by an element rupturing a wall of the reservoir.

4. The biochemical assay device of claim 1, wherein the flow path is a porous or capillary structure of the substrate for capillary transport of the washing liquid.

5. The biochemical assay device of claim 1, wherein a microfluidic system is provided for transport of sample fluid to the finite zone.

6. The biochemical assay device of claim 1, wherein an adsorbing element is arranged on the flow path downstream the finite zone for taking up liquid waste.

7. The biochemical assay device of claim 1, wherein the substrate is a solid phase chromatographic layer on a polymer or metal support.

8. The biochemical assay device of claim 1, wherein the substrate comprises aluminium oxide or silica or a reversed-phase material.

9. The biochemical assay device of claim 1, wherein the size of the molecule is less than the size of the analyte.

10. The biochemical assay device of claim 1, wherein the molecule is polar.

11. The biochemical assay device of claim 1, wherein the conjugate is a labelled organic or inorganic molecule.

12. The biochemical assay device of claim 1, wherein the conjugate reagent contains a boronic acid dye, a chelating group, a peptide epitope, or an oligonucleotide.

13. The biochemical assay device of claim 1, wherein the conjugate reagent has a high coefficient of partition for the washing liquid compared to the substrate.

14. The biochemical assay device of claim 1, wherein the washing liquid is an organic solvent, a mixture of water and a miscible organic solvent, or an aqueous solution.

15. The biochemical assay device of claim 1, wherein the washing liquid is buffered at such pH that the analyte sticks to the substrate and the binding reaction of the conjugate still occurs.

16. The biochemical assay device of claim 1, wherein the washing liquid contains a surfactant.

17. The biochemical assay device of claim 1, wherein the biological sample is blood.

18. The biochemical assay device of claim 1, wherein the biological sample is whole blood.

19. The biochemical assay device of claim 1, wherein the target analyte is haemoglobin.

20. The biochemical assay device of claim 1, wherein the target analyte is glycated haemoglobin.

21. The biochemical assay device of claim 1, wherein the substrate is impregnated with a haemolysing agent.

22. The biochemical assay device of claim 21, wherein said haemolysing agent is tetradecyltrimetylammonium bromide.

23. The biochemical assay device of claim 1, wherein said device is disposable.

24. An analytical test element for determining the ratio of glycated to total haemoglobin in a blood sample comprising:
    a substrate comprising a strip that non-specifically binds haemoglobin,
    a finite zone formed as one spot on the substrate defining a sample application area, a reagent zone and detection area,
    a non-immobilized conjugate reagent dried in the finite zone for labelling glycated haemoglobin, said conjugate reagent being a molecule other than a protein and being capable of specific binding to glycated haemoglobin but remaining unbound to the substrate, and
    a flow path for transporting a washing liquid through the finite zone and washing an excess of unbound conjugate away from the finite zone, wherein
    the finite zone is located in correspondence to a detector for detecting labelled haemoglobin and total haemoglobin.

25. The analytical test element of claim 24, wherein the conjugate comprises boronic acid dye.

26. A device for processing an analytical test element according to claim 24.

27. A process for determining at least one target analyte in a biochemical sample, comprising:
    a) providing a substrate, the substrate comprising a strip comprising a finite zone formed as one spot on the substrate defining a sample application area, a reagent zone and detection area, the substrate itself being capable of non-specifically binding at the test zone at least the target analyte and eventually other constituents contained in the sample,
    b) providing a non-immobilized conjugate reagent in the finite zone for labelling the analyte, said conjugate reagent being a molecule other than a protein and being capable of specific binding to the analyte but remaining unbound to the substrate,
    c) applying the sample in the finite zone of the substrate,
    d) transporting a washing liquid through the finite zone and washing an excess of unbound conjugate reagent away from the finite zone, and
    e) detecting the labelled analyte in the finite zone, which can be located in correspondence to the detector.

28. The process of claim 27, wherein blood is used as a sample and non-glycated haemoglobin and glycated haemoglobin are adsorbed on the substrate, the conjugate reagent being bound to the glycated haemoglobin.

29. The process of claim 28, wherein said blood is whole blood.

30. The process of claim 27, wherein total haemoglobin and glycated haemoglobin are photometrically detected at different respective wavelengths and that the ratio of glycated to total haemoglobin is determined.

31. A measuring device for processing the biochemical assay device according to claim 1.

* * * * *